(12) United States Patent
Rice et al.

(10) Patent No.: US 11,608,516 B2
(45) Date of Patent: Mar. 21, 2023

(54) METHOD FOR DETERMINATION OF DIVERSITY AND VIABILITY THRESHOLDS USED TO ASSESS MICROORGANISMS IN PROCESS SAMPLES

(71) Applicant: ECOLAB USA INC., St. Paul, MN (US)

(72) Inventors: Laura E. Rice, St. Charles, IL (US); Liliya Lund, Warrenville, IL (US)

(73) Assignee: ECOLAB USA INC., St. Paul, MN (US)

( * ) Notice: Subject to any disclaimer, the term of this patent is extended or adjusted under 35 U.S.C. 154(b) by 84 days.

(21) Appl. No.: 14/687,017

(22) Filed: Apr. 15, 2015

(65) Prior Publication Data

US 2016/0304931 A1    Oct. 20, 2016

(51) Int. Cl.
| | | |
|---|---|---|
| C12Q 1/06 | (2006.01) | |
| C12Q 1/689 | (2018.01) | |
| G01N 33/18 | (2006.01) | |
| G01N 33/569 | (2006.01) | |

(52) U.S. Cl.
CPC .............. *C12Q 1/06* (2013.01); *C12Q 1/689* (2013.01); *G01N 33/1826* (2013.01); *G01N 33/56911* (2013.01)

(58) Field of Classification Search
CPC ...... C12Q 1/06; C12Q 1/689; G01N 33/1826; G01N 33/56911
See application file for complete search history.

(56) References Cited

U.S. PATENT DOCUMENTS

| | | | |
|---|---|---|---|
| 5,281,537 A | 1/1994 | Robertson et al. | |
| 5,928,875 A | 7/1999 | Breen et al. | |
| 6,054,267 A | 4/2000 | Short | |
| 6,143,496 A | 11/2000 | Brown et al. | |
| 6,372,139 B1* | 4/2002 | Habets | C02F 9/00 210/605 |
| 6,849,395 B2 | 1/2005 | Short et al. | |
| 7,018,793 B1 | 3/2006 | Short et al. | |
| 7,931,813 B2* | 4/2011 | Asokan | A61L 2/02 205/722 |
| 7,949,432 B2 | 4/2011 | Rice | |
| 7,981,679 B2 | 7/2011 | Rice | |
| 8,012,758 B2 | 9/2011 | Enzien et al. | |
| 8,613,837 B2* | 12/2013 | Rice | D21H 21/04 162/198 |
| 9,290,802 B2* | 3/2016 | Rice | C12Q 1/686 |
| 9,295,745 B2* | 3/2016 | Rice | A61L 2/24 |
| 2002/0031771 A1 | 3/2002 | Short et al. | |
| 2010/0314316 A1* | 12/2010 | Yin | A01N 37/30 210/636 |
| 2012/0152814 A1* | 6/2012 | Lean | C02F 1/385 210/202 |
| 2013/0186582 A1 | 7/2013 | Rice et al. | |
| 2014/0000346 A1* | 1/2014 | Hoek | B01D 61/025 73/38 |
| 2014/0141443 A1 | 5/2014 | Rice et al. | |
| 2016/0176735 A1* | 6/2016 | Balasubramanian | C02F 1/50 210/729 |
| 2016/0176815 A1* | 6/2016 | Li | C07C 409/24 562/6 |

FOREIGN PATENT DOCUMENTS

| | | | | |
|---|---|---|---|---|
| JP | 2002242098 A | * | 8/2002 | ............ D21H 23/02 |
| WO | 2004042082 A1 | | 5/2004 | |
| WO | 2004046375 A2 | | 6/2004 | |
| WO | 2005042082 | | 5/2005 | |
| WO | 2007024295 A3 | | 3/2007 | |
| WO | 2008061193 A3 | | 5/2008 | |
| WO | 2013/112656 A1 | | 8/2013 | |
| WO | WO 2014/015044 A1 | | 1/2014 | |
| WO | 2015/100123 A1 | | 7/2015 | |

OTHER PUBLICATIONS

International Search Report and Written Opinion for Application No. PCT/US2016/027484 dated Aug. 7, 2016.
"website http://www.eurogentec.com/file-browser.html", website http://www.eurogentec.com/file-browser.html on Jan. 19, 2012)., Jan. 19, 2012 and Apr. 16, 2015.
Website http://www.illumina.com/technology/sequencing_technology.ilmn, http://www.illumina.com/technology/sequencing_technology.ilmn (as accessed on Dec. 23, 2013)., Dec. 23, 2013.
Website: http://www.lifetechnologies.com/us/en/home/life-science/sequencing/next-generation-sequencing/ion-torrent-next-generation-sequencing-technology.html (as accessed Dec. 23, 2013 and Apr. 28, 2015.
Website: http://bitesizebio.com/13546/sequencing-by-synthesis-explaining-the-illumina-sequencing-technology/; accessed on Dec. 23, 2013 and Apr. 28, 2015.
Conway, et al., Phyloproteomics: Species Identification of Enterobacteriaceae using Matrix-Assisted Laser Desorption/ Ionization Time-of Flight Mass Spectrometry, J. Mol. Microbiol. Biotechnol. 3: 103-112, (2001).
Life Technologies Corporation website: http://gtc.soe.ucsc.edu/content/solid-technology-overview (as accessed on Dec. 23, 2013).
sales brochure: See the Difference Discover the Quality Genome, (2010).
Flynn, "The Nalco Water Handbook (3rd Edition)", McGraw Hill (2009) in general and in particular pp. 32.1-32.44., 2009, 32.1-32.44.
Mullis, et al., "Article Specific Synthesis of DNA in Vitro via a Polymerase-Catalyzed Chain Reaction", Methods in Enzymology, vol. 155, pp. 335-350 (1987), 1987, vol. 155, pp. 335-350.
Muyzer, et al., Scientific Article: Profiling of Complex Microbial Populations by Denaturing Gradient Gel Electrophoresis Analysis of Polymerase Chain Reaction-Amplified Genes Coding for 16S rRNA, Applied and Environmental Microbiology, vol. 59, No. 3, pp. 695-700, Mar. 1993.

(Continued)

*Primary Examiner* — Regina M Yoo
(74) *Attorney, Agent, or Firm* — Merchant & Gould P.C.

(57) ABSTRACT

The invention is directed towards methods and compositions for identifying the specific microorganisms present in a particular potion of a water process system. The method involves obtaining a sample from the process and determining if a problematic organism exceeds an acceptable threshold. If so a remedial bio-control procedure can be applied long before any unwanted defects or problems occur.

15 Claims, 3 Drawing Sheets

(56) References Cited

OTHER PUBLICATIONS

Pavlovic, et al., "Application of MALDI-TOF MS for the Identification of Food Borne Bacteria,", Open Microbiol J.; 7: 135-141 (2013)., 2013, Open Microbiol J.; 7: 135-141.
Ronaghi, "Article—Pyrosequencing Sheds Light on DNA Sequencing", Genome Research, 11:3-11 (2001) which can be found at http://genome.cshlp.org/content/11/1/3.full.html#ref-list-1 (as accessed on Dec. 23, 2013)., Dec. 23, 2013.
Saiki, et al., "Article Primer Directed Enzymatic Amplification of DNA with a Thermostable DNA Polymerase", Science, vol. 239, pp. 487-491 (1988), 1988, Science, vol. 239, pp. 487-491.
Vogelstein, et al., scientific article Digital PCR, Proc. Natl. Acad. Sci. USA, Genetics, vol. 96, pp. 9236-9241, Aug. 1999.
Extended European Search Report for Application No. 16780726.2 dated Oct. 24, 2018.
Smook, Handbook for Pulp & Paper Technologists, pp. 337-339, (1982).
Blanco et al., "Slime problems in the paper and board industry," Appl Microbial Biotechnol, vol. 46, pp. 203-208 (1996).
Directory of Microbicides for the Protection of Materials A Handbook, edited by Wilfried Paulus, published by Springer Chapter 5.15 Pulp & Paper by G. Corbel, pp. xvi-xvii (contents), 377-409 (2003).
Kolari, "New research gives breakthrough in cutting slime and corrosion risk on PM," World Pulp & Paper, pp. 51-54 (2011).
Maukonen et al., "Methodologies for the characterization of microbes in industrial environments: a review," J Ind Microbiol. Biotechnol., vol. 30, pp. 327-356 (2003).

\* cited by examiner

METHOD FOR DETERMINATION OF DIVERSITY AND VIABILITY THRESHOLDS USED TO ASSESS MICROORGANISMS IN PROCESS SAMPLES

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

The present invention relates generally to compositions of matter, apparatuses and methods useful in determining diversity and viability thresholds. The threshold may be used to determine if microorganisms are contributing to process efficiency problems or product quality problems. The threshold is also useful in identifying where a particular microorganism entered a process stream and/or where it proliferated.

The presence of unwanted microorganisms in an industrial process stream can lead to a number of problems such as deposition on equipment surfaces, impaired machine performance, loss of production efficiency, and off-spec end products. Being able to accurately identify which organisms are proliferating and how they are doing so can greatly aid in addressing these problems.

For example, in papermaking systems microbial growth can be quite harmful and costly. The growth of microorganisms on equipment surfaces can lead to the formation of deposits that slough and contribute to sheet defects and holes. Contaminated shower water treatments or process water can lead to the growth of microbes on felts which commonly result in the formation of plugs on the felts. These plugs in turn cause a number of problems most notably the impairment of water removal from paper web. As a result microbial growth can result in an excessive and costly need for multiple boil-outs and cleanings of felts or other papermaking equipment. These problems can be compounded when an incorrect determination of which microorganisms occurs because this can result in a requirement for aggressive chemical treatment which may lead to reduction in useful life of the felt, further degrade the quality of the paper, further impact process equipment, and/or may not even control the underlying microbial infestation. Moreover incorrectly distinguishing between biologically caused problems and mechanical or chemical caused problems can further result in inadequate, wasteful, and possibly counterproductive efforts.

A number of prior art methods are known for identifying which microorganisms are present in a papermaking system. These methods however are particularly deficient when applied to paper sheets or felts. Some of the prior art methods such as U.S. Pat. Nos. 8,012,758, 7,981,679, and 7,949,432 detect various effects in the fluids of the papermaking system produced by living microbiological organisms. Other methods such as U.S. Pat. No. 5,281,537 rely on obtaining a sample of living microorganism contaminant and growing more of it so as to perform various analyses. In the context of paper sheets and felts however these methods are particularly inadequate as by the time samples of the felt or paper are taken they no longer contain sufficient (or any) live organisms to culture or any of the chemical products that they produce. Also items of the papermaking system (such as paper sheets and felts) that are downstream from the heating or drying sections will have had all the defect causing microorganisms killed off after they have already caused the defects. Alternative methods that do not rely on the presence of live organisms also tend to be deficient because they often produce false positives. For example ninhydrin (which is used to detect primary or secondary amines) and IR spectroscopy often produce false positives or negatives because they detect materials that may have non-biological origins (such as chemical additives or contamination).

Thus it is clear that there is clear utility in novel methods and compositions for the proper identification of microorganisms present on industrial process streams and equipment. The art described in this section is not intended to constitute an admission that any patent, publication or other information referred to herein is "Prior Art" with respect to this invention, unless specifically designated as such. In addition, this section should not be construed to mean that a search has been made or that no other pertinent information as defined in 37 CFR § 1.56(a) exists.

BRIEF SUMMARY OF THE INVENTION

To satisfy the long-existing but unsolved needs identified above, at least one embodiment of the invention is directed towards a method of anticipating a microorganism caused problem in a water process system. The method comprises the steps of: measuring the overall microorganism population in at least a portion of the system; measuring the amount of at least one subgroup of microorganism population relative to the overall microorganism population; determining if the amount of at least one subgroup of microorganisms exceeds a threshold, the threshold being at least one of a pre-determined: absolute amount of the subgroup of microorganisms, a relative amount of the subgroup of microorganisms, and any combination thereof; and optionally enacting a bio-control procedure to remediate the presence of the at least one subgroup of microorganisms.

The subgroup of microorganisms may comprise filamentous bacteria. The subgroup of microorganisms may comprises *Spirogyra, Cladophora, Pithophora, O. Siphonocladales pithophora pithophora, Ulvibacter litoralis, Vetellibacter vladivostokensis, Weeksella virosa, Fucobacter, Gelidbacter, Ornithobacterium rhinotracheale, Riemerella cohambina, Flavobacterium psychrofilum, Ctyophaga succinicans, Vladibacter, Pfeifferella, Bacillus aquatilllis, Flexibacter marinus, Flavobacterium odoratum, Microscilla, Flexithrix, Capnocytophaga, Taxeobacter, Sporocytophaga, Saprospira, Chryseobacterium, Hymenobacter*, and any combination thereof. The threshold may be that the subgroup of microorganisms is measured to be at an amount of at least 5-90% of the overall microorganism population.

The at least one measurement may be taken by one process selected from the list consisting of: Chain Termination Sequencing, Denaturing Gradient Gel Electrophoresis (DGGE), Digital Polymerase Chain Reaction, DNA Based Analysis, Ion Torrent Semiconductor Sequencing, MALDI, MALDI-TOF, Mass Spectrometry, PCR Analysis, Pyrosequencing, qPCR Analysis, Sequencing by Oligonucleotide Ligation and Detection, Sequencing by Synthesis, measurement of antibodies associated with one or more microorganisms, measurement of hormones associated with one or more microorganisms, measurement of secretions associated with one or more microorganisms, measurement of proteins associated with one or more microorganisms, measurement of organic molecules associated with one or more microorganisms, measurement of molecules associated with one or more microorganisms, fluorescent phages, cell sorters, and any combination thereof.

The method may further comprise identifying an input source that is the cause of the at least one subgroup of microorganism population. The input source may be feed water, raw materials, fiber, or dyes from one source selected from the group consisting of: municipal water, tap water, pond water, sea water, lake water, filtered water, desalinated water, recirculated water, wastewater, distilled water, condensed boiler water, cooling water, titanium dioxide, clay, process additives, polymers, dyes, optical brightening agents, and any combination thereof. The method may further comprising the step of identifying the water source the subgroup of microorganisms comes from and enacting a bio-control procedure to remediate the presence of the at least one subgroup of microorganisms only subsequent to and no later than 1 week of the introduction of water from the water source the subgroup of microorganisms comes from.

The water process system may be one or more stages of one item selected from the group consisting of: papermaking, cooling water, boiler water, food manufacturing, beverage manufacturing, ore processing, alumina processing, biodiesel manufacturing, distillation, petrochemical refining, petrochemical synthesis, polymer synthesis, plastic manufacturing, wastewater processing, laundry, warewashing, water treatment, solid-liquid separation, and any combination thereof. The method may further comprise the step of recording the identified organism into a format which can be stored and/or transmitted.

The method may further comprise the step of conducting a biocidal program associated with remedying the identified organism. The method may further comprise taking at least one measurement from a sample product of the process system. The sample may be so desiccated that there are little or no living organisms on it.

Additional features and advantages are described herein, and will be apparent from, the following Detailed Description.

BRIEF DESCRIPTION OF THE DRAWINGS

A detailed description of the invention is hereafter described with specific reference being made to the drawings in which.

For the purposes of this disclosure, like reference numerals in the figures shall refer to like features unless otherwise indicated. The drawings are only an exemplification of the principles of the invention and are not intended to limit the invention to the particular embodiments illustrated.

DETAILED DESCRIPTION OF THE INVENTION

Definitions

Figure 1:
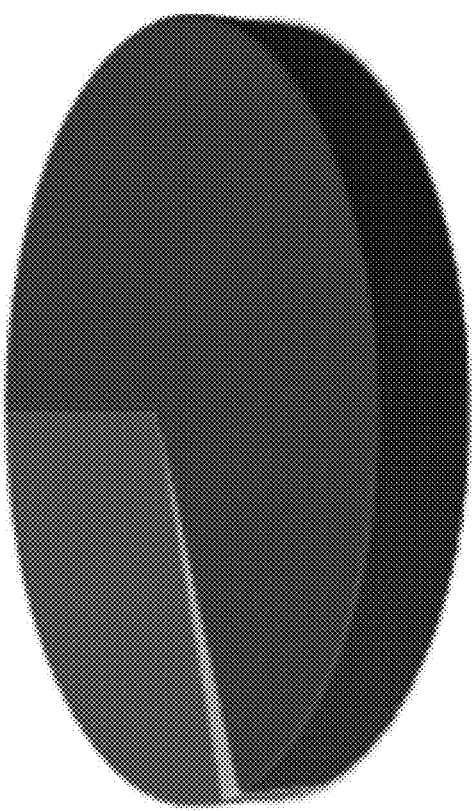
FIG. 1 illustrates pie charts of qPCR analysis of felts from a paper machine with no felt permeability problems (PM2 pickup felt) and felt samples from the machine with felt permeability problems (PM1 pickup felt).
Figure 1:
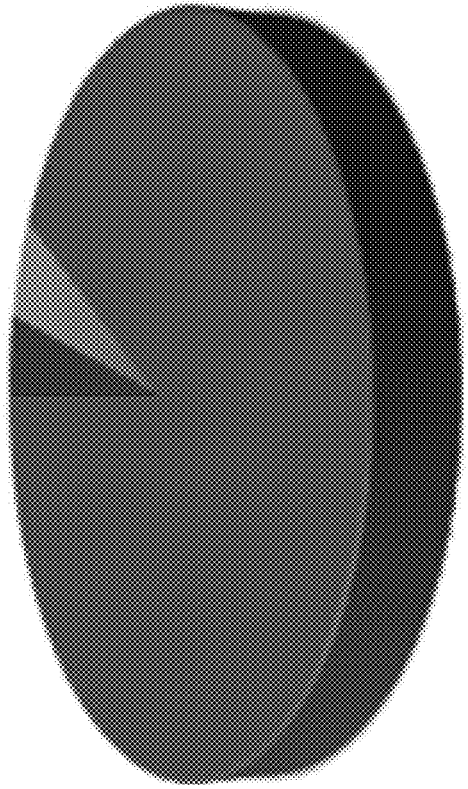

The following definitions are provided to determine how terms used in this application, and in particular how the claims, are to be construed. The organization of the definitions is for convenience only and is not intended to limit any of the definitions to any particular category.

"Chain Termination Sequencing" means a method which requires a single-stranded DNA template, a DNA primer, a DNA polymerase, normal deoxynucleosidetriphosphates (dNTPs), and modified nucleotides (dideoxyNTPs) that terminate DNA strand elongation. These chain-terminating nucleotides lack a 3'-OH group required for the formation of a phosphodiester bond between two nucleotides, causing DNA polymerase to cease extension of DNA when a ddNTP is incorporated. The ddNTPs may be radioactively or fluorescently labelled for detection in automated sequencing machines. In some cases Chain termination sequencing may involve the synthesis of new strands of DNA complementary to a single-stranded template (step I). The template DNA is supplied with a mixture of all four deoxynucleotides, four dideoxynucleotides—each labeled with a different color fluorescent tag, and DNA polymerase (step II). As all four deoxynucleotides are present, chain elongation proceeds until, by chance, DNA polymerase inserts a dideoxynucleotide. The result is a new set of DNA chains all of different lengths (step III). The fragments are then separated by size using gel electrophoresis (step IV). As each labeled DNA fragment passes a detector at the bottom of the gel, the color is recorded. The DNA sequence is then reconstructed from the pattern of colors representing each nucleotide sequence (step V).

"Defect" means an unwanted attribute of an item associated with an industrial process or process stream, in the context of a papermaking process it includes but is not limited to one or more plugs on a felt, and such attributes of paper sheet as holes, discoloration, streaks, spots, translucent spots, and any combination thereof.

"Denaturing Gradient Gel Electrophoresis (DGGE)" means a form of electrophoresis which uses a chemical gradient to denature the sample as it moves across an acrylamide gel. DGGE can be applied to nucleic acids such as DNA and RNA, thus allowing the user to assess the number of different DNA/RNA sequences present in a sample. Representative example can be found in the Scientific Article: *Profiling of Complex Microbial Populations by Denaturing Gradient Gel Electrophoresis Analysis of Polymerase Chain Reaction-Amplified Genes Coding for 16S rRNA*, by G. Muyzer et al., Applied and Environmental Microbiology, Vol. 59, No. 3, pp. 695-700, March (1993).

"Digital Polymerase Chain Reaction" or (digital PCR, DigitalPCR, dPCR, or dePCR) means a refinement of conventional polymerase chain reaction methods that can be used to directly quantify and clonally amplify nucleic acids including DNA, cDNA or RNA. The key difference between dPCR and traditional PCR lies in the method of measuring nucleic acids amounts, with the former being a more precise method than PCR. PCR carries out one reaction per single sample. dPCR also carries out a single reaction within a sample, however the sample is separated into a large number of partitions and the reaction is carried out in each partition individually. This separation allows a more reliable collection and sensitive measurement of nucleic acid amounts. Representative examples are described in U.S. Pat. No.

6,143,496 and in the scientific article *Digital PCR*, by B. Vogelstein et al., Proc. Natl. Acad. Sci. USA, Genetics, Vol. 96, pp. 9236-9241, August (1999).

"DNA Based Analysis" means an method of analyzing DNA, including but not limited to qPCR, PCR, digital PCR, ion semiconductor sequencing, pyrosequencing, sequencing by synthesis, sequencing by litigation, chain terminating sequencing, and any combination thereof.

"Felt" means a belt made of interweaved wool or any other fiber used in a papermaking process which functions as a conveyer of materials wherein the interweaved fibers define a plurality of lumens through which water or other fluids may pass. Felts may also provide cushioning between press rolls and may also be a medium used to remove water from papermaking materials. Felts include but are not limited to bottom felts, bottom board felts, cylinder tissue wet felts, drier felts, endless felts, pickup felts, suction pickup felts, Harper top felts, and top felts.

"Ion Torrent Semiconductor Sequencing" means a method of DNA sequencing based on the detection of hydrogen ions that are released during the polymerization of DNA. This is a method of "sequencing by synthesis", during which a complementary strand is built based on the sequence of a template strand, a representative example of this is described at the website: http://www.lifetechnologies.com/us/en/home/life-science/sequencing/next-generation-sequencing/ion-torrent-next-generation-sequencing-technology.html (as accessed on Dec. 23, 2013).

"MALDI" means Matrix-Assisted Laser Desorption/Ionization, a form of Mass Spectrometry used to identify biomolecules (biopolymers such as DNA, proteins, peptides and sugars) and large organic molecules (such as polymers, dendrimers and other macromolecules), it typically involves ablation into a gaseous ionic state of a sample by pulsing a laser against it and then analyzing the sample by mass spectrometry. Representative examples of using MALDI to identify organisms are described in the scientific articles:

*Phyloproteomics: Species Identification of Enterobacteriaceae using Matrix-Assisted Laser Desorption/Ionization Time-of Flight Mass Spectrometry,* by G. C. Conway, et al., J. Mol. Microbiol. Biotechnol. 3: 103-112, (2001),

*Real-time identification of bacteria and Candida species in positive blood culture broths by matrix-assisted laser desorption ionization-time of flight mass spectrometry,* by A. Ferroni, et al., J Clin Microbiol., 48(5), 1542-1548, (2010 May), and

*Application of MALDI-TOF MS for the Identification of Food Borne Bacteria,* by M. Pavlovic, et al., Open Microbiol J.; 7: 135-141 (2013).

"Mass Spectrometry" or (MS) means an analytical chemistry technique used to identify the amount and type of chemicals present in a sample by measuring the mass-to-charge ratio and abundance of gas-phase ions, it is more thoroughly described in the textbook: *Mass Spectrometry—A Foundation Course,* by K Downard, Cambridge UK: Royal Society of Chemistry (2004).

"Microorganisms" means any organism small enough to insinuate itself within, adjacent to, on top of, or attached to equipment used in an industrial process or stream such as but not limited to a papermaking process, it includes but is not limited to those organisms so small that they cannot be seen without the aid of a microscope, collections or colonies of such small organisms that can be seen by the naked eye but which comprise a number of individual organisms that are too small to be seen by the naked eye, as well as one or more organisms that can be seen by the naked eye, it includes but is not limited to any organism whose presence, in some way impairs a water process system, it also includes but is not limited to those so identified microorganisms described in the textbooks: *Brock Biology of Microorganisms* (14th Edition) Hardcover, by Michael T. Madigan et al., Benjamin Cummings Publisher, (2014) and *The Prokaryotes: Vol 7: Proteobacteria: Delta and Epsilon Subclasses. Deeply Rooting Bacteria,* by Dworkin, M., Falkow, S. Springer Science and Business Media, (2006).

"Paper Product or Paper Sheet" means any formed fibrous structure end product of a papermaking process traditionally, but not necessarily, comprising cellulose fibers. Examples of such end products include but are not limited to facial tissue, bath tissue, table napkins, copy paper, printer paper, writing paper, notebook paper, newspaper, paper board, poster paper, bond paper, cardboard, and the like.

"Papermaking Process" means any portion of a method of making paper products from pulp comprising forming an aqueous cellulosic papermaking furnish, draining the furnish to form a sheet and drying the sheet. The steps of forming the papermaking furnish, draining and drying may be carried out in any conventional manner generally known to those skilled in the art. The papermaking process may also include a pulping stage, i.e. making pulp from a lignocellulosic raw material and bleaching stage, i.e. chemical treatment of the pulp for brightness improvement, it may also include but is not limited one or more of such steps as pulping, digesting, refining, drying, calandering, pressing, crepeing, dewatering, and bleaching, papermaking is further described in the reference *Handbook for Pulp and Paper Technologists,* 3rd Edition, by Gary A. Smook, Angus Wilde Publications Inc., (2002) and *The Nalco Water Handbook* (3rd Edition), by Daniel Flynn, McGraw Hill (2009) in general and in particular pp. 32.1-32.44.

"PCR Analysis" means polymerase chain reaction analysis.

"Plug" means a solid, semisolid, viscous, and/or other deposit of material positioned within the lumens of a felt. Plugs may inhibit the flow of material through the lumens, and/or may impair any other functionality of a felt.

"Primer" means a composition of matter, typically a short strand of nucleotides, known to be complementary to specific sections of DNA and serve as a starting point for synthesis of a nucleotide chain complementary to DNA adjacent to the specific section of DNA.

"Probe" means a composition of matter constructed and arranged to bind to a targeted section of DNA and which can be readily detected when so bound and thereby be used to indicate the presence or absence of the targeted section of DNA.

"Pyrosequencing" means a method of DNA sequencing (determining the order of nucleotides in DNA) based on the "sequencing bysynthesis" principle. It differs from Sanger sequencing, in that it relies on the detection of pyrophosphate release on nucleotide incorporation, rather than chain termination with dideoxynucleotides. The desired DNA sequence is able to be determined by light emitted upon incorporation of the next complementary nucleotide by the fact that only one out of four of the possible A/T/C/G nucleotides are added and available at a time so that only one letter can be incorporated on the single stranded template (which is the sequence to be determined). A representative example can be found in the Article *Pyrosequencing Sheds Light on DNA Sequencing,* by Mostafa Ronaghi, Genome Research, 11:3-11 (2001) which can be found at http://genome.cshlp.org/content/11/1/3.full.html#ref-list-1 (as accessed on Dec. 23, 2013).

"qPCR Analysis" means quantitative and/or qualitative polymerase chain reaction analysis.

"Sequencing by Oligonucleotide Ligation and Detection" means a way of generating hundreds of millions to billions of small sequence reads at one time. This is achieved by attaching small fragments of an unknown sequence to magnetic beads which then undergo immersion PCR. Representative examples can be found at the website: http://gtc.soe.ucsc.edu/content/solid-technology-overview (as accessed on Dec. 23, 2013). And the sales brochure: *See the Difference Discover the Quality Genome by* Life Technologies Corporation (2010).

"Sequencing by Synthesis" means a technique used to determine the series of base pairs in DNA, also known as DNA sequencing. This sequencing method is based on reversible dye-terminators that enable the identification of single bases as they are introduced into DNA strands. Representative examples can be found at the websites: http://nxseq.bitesizebio.com/articles/sequencing-by-synthesis-explaining-the-illumina-sequencing-technology/ and http://www.illumina.com/technology/sequencing_technology.ilmn (as accessed on Dec. 23, 2013).

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Othmer Encyclopedia of Chemical Technology*, 5th Edition, (2005), (Published by Wiley, John & Sons, Inc.) this definition shall control how the term is to be defined in the claims. All illustrated chemical structures also include all possible stereoisomer alternatives.

At least one embodiment of the invention is directed towards a method of determining the threshold at which a change in the diversity index warrants a change in bio-controls of a water process system. As described for example in U.S. patent applications Ser. Nos. 13/374,949, 13/550,748, and 14/138,526 a diversity index is a useful tool in determining the potential of a microorganism caused defect or problem. Moreover identifying specific microorganism infestations can help to indicate which sorts of defect or problems may result. Diversity indices rely on identifying a threshold of change in the index which is a pre-cursor to such a defect or problem. Thus there is great utility and value in methods for determining the threshold at which a microorganism is considered to be the main cause of the problem.

In at least one embodiment the method of determining if a change in the diversity index indicates a potential future or present problem or defect comprises: determining the microbial diversity present in a water process system, determining the abundance of one/some/each detected microorganism relative to the total population, determining if the abundance of the total population is indicative that microorganism are likely to cause a defect or problem, determining if the relative or absolute abundance of any one or some microorganisms exceed the predetermined threshold, and optionally enacting a biocontrol protocol or procedure to eliminate/address the microorganism(s).

In at least one embodiment threshold value is identified using historic microbial and process efficiency and quality data that correlate the level of abundance associated with production issues and not merely variability in the analysis. This value may vary from one process application to another as some systems may be able to tolerate higher levels of microbial contamination before the microbes cause a negative impact on efficiency or product quality. In at least one embodiment subsequent analysis is used to confirm that the treatment has reduced the population below the predetermined threshold to provide assurance that production or quality problems related to that microorganism's growth cease to occur.

In at least one embodiment to accomplish one or more of the steps of the above process one or more methods, compositions, and apparatuses from any one, some or all of the following references are used: U.S. patent application Ser. Nos. 13/289,547, 13/374,949, 13/550,748, 14/138,526, U.S. Pat. Nos. 8,613,837, 7,018,793, 6,849,395, 6,054,267, US Published Patent Application: 2002/0031771, 2013/0186582, and International Patent Documents: WO 2008/061193 A2, WO 2007/024295 A2, WO 2004/046375 A2, and WO 2004/042082 A1.

In at least one embodiment the method includes the step of measuring a rise in the amount of filamentous bacteria/microorganisms relative to the overall microbial population by between up to 5% and up to 90% or more. In at least one embodiment the method includes the step of measuring a rise in the amount of at least one organism relative to the overall microbial population by between 5-90% selected from the list consisting of: *Spirogyra, Cladophora, Pithophora, O. Siphonocladales pithophora pithophora, Ulvibacter litoralis, Vetellibacter vladivostokensis, Weeksella virosa, Fucobacter, Gelidbacter, Ornithobacterium rhinotracheale, Riemerella cohambina, Flavobacterium psychrofilum, Ctyophaga succinicans, Vladibacter, Pfeifferella, Bacillus aquatilllis, Flexibacter marinus, Flavobacterium odoratum, Microscilla, Flexithrix, Capnocytophaga, Taxeobacter, Sporocytophaga, Saprospira, Chryseobacterium, Hymenobacter* and any combination thereof. In at least one embodiment the method includes the step of measuring a rise in the amount of at least one organism relative to the overall microbial population by between 5-90%, the organism being one of those described or mentioned in the textbook *The Prokaryotes: Vol 7: Proteobacteria: Delta and Epsilon Subclasses. Deeply Rooting Bacteria,* by Dworkin, M., Falkow, S. Springer Science and Business Media, (2006).

In at least one embodiment the change in the diversity index is used to identify which process input is the potential or actual cause of a problem or defect. Such process inputs include but are not limited to water sources, material sources, and specific pieces of equipment. For example a process water system include a number of new and/or recirculating water sources which may include but are not limited to one or more kinds of: pond water, sea water, lake water, filtered water, desalinated water, recirculated water, wastewater, distilled water, condensed water, condensed boiler water, cooling water, and any combination thereof. In addition the process system may have introduced into it one or more raw materials or partially processed materials. Also sometimes one or more pieces of equipment or pipes/flow lines are or are not used in a given operation or particular surfaces thereof do or do not come into contact with the process subject. If a particular problem is the result of an organism coming from only one or some of those process inputs, it would be efficient to only use a the bio-control process when those process inputs are being used or target treatment and/or add additional treatment to the contaminated input. Moreover it is more efficient to enact the bio-control when a threshold is exceeded as opposed to waiting until so much of the problem organism accumulates/breeds as to actually cause a defect or problem.

In at least one embodiment the method of measuring some or all of the diversity index using data uses one or more of: Chain Termination Sequencing, Denaturing Gradient Gel Electrophoresis (DGGE), Digital Polymerase Chain Reaction, DNA Based Analysis, Ion Torrent Semiconductor Sequencing, MALDI, MALDI-TOF, Mass Spectrometry, PCR Analysis, Pyrosequencing, qPCR Analysis, Sequencing by Oligonucleotide Ligation and Detection, Sequencing by Synthesis, measurement of antibodies associated with one or more microorganisms, measurement of hormones associated with one or more microorganisms, measurement of secretions associated with one or more microorganisms, measurement of proteins associated with one or more microorganisms, measurement of organic molecules associated with one or more microorganisms, measurement of molecules associated with one or more microorganisms, fluorescent phages, cell sorters, and any combination thereof.

In at least one embodiment the process water system may be but is not limited to one or more process stages of one or more of: papermaking, cooling water, boiler water, food manufacturing, beverage manufacturing, ore processing, alumina processing, biodiesel manufacturing, distillation, petrochemical refining, petrochemical synthesis, polymer synthesis, plastic manufacturing, wastewater processing, laundry, warewashing, water treatment, solid-liquid separation, and any combination thereof.

In at least one embodiment the method can be applied to the detection of microorganisms in a variety of samples taken from a manufacturing system. These samples include deposits on equipment surfaces, water or fluid samples, and/or whole pieces or partial fragments of intermediate or end stage products of the process. It may analyze defects in the product sample or the product sample as a whole.

In at least one embodiment a highly sensitive and rapid detection method is provided for microorganisms located in intermediate or end products of a manufacturing process. The method includes analysis of materials present in samples extracts. These samples may be highly desiccated and may contain little or no live samples of the contaminating microorganisms. Some prior art methods of utilizing DNA analysis include WO 2005/042082 which describes an in situ method utilizing probes to determine the presence or absence of a microorganism. In situ methods however are not applicable to paper sheets or felts as they are dried out when sampled. Also the in situ method involves applying the probes during cell division of the microorganisms which is not possible on paper sheets or felts with little or no more living organisms on them. In at least one embodiment the DNA based analysis involves the use of probes.

In at least one embodiment the DNA based analysis involves the use of PCR primers to detect the presence or absence of microorganisms. U.S. Pat. No. 5,928,875 describes the use of PCR primers to detect the presence or absence of spore forming bacteria. In at least one embodiment the primer is targeted towards a part of a DNA strand which is highly conserved among a group of organisms. As a result, detecting the presence of that particular part of DNA is definitive proof of the presence a specific organism. PCR analysis is of particular use in analyzing samples due to the difficultly of correctly identifying its contaminating microorganisms because they lack viable organisms for traditional plating methods or ATP measurements.

In at least one embodiment the PCR analysis involves utilizing one or more of the methods described in the Article Primer Directed Enzymatic Amplification of DNA with a Thermostable DNA Polymerase, by Randall Saiki et al., Science, Volume 239, pp. 487-491 (1988). In at least one embodiment the PCR analysis involves utilizing one or more of the methods described in the Article Specific Synthesis of DNA in Vitro via a Polymerase-Catalyzed Chain Reaction, by Kary Mullis et al., Methods In Enzymology, Volume 155, pp. 335-350 (1987).

In at least one embodiment the PCR analysis is a qPCR analysis as described in Trade Brochure qPCR guide, prefaced by Jo Vandesompele, (as downloaded from website http://www.eurogentec.com/file-browser.html on Jan. 19, 2012). In at least one embodiment the method is a quantitative qPCR analysis. In at least one embodiment the method is a qualitative qPCR analysis.

As illustrated in at least one embodiment, once DNA is extracted from the sample, using any of the DNA extraction kits available commercially, it can be analyzed in real-time using a PCR approach such as a Quantitative PCR approach. Quantitative PCR utilizes the same methodology as PCR, but it includes a real-time quantitative component. In this technique, primers are used to target a DNA sequence of interest based on the identity of the organism or function of a specific gene. Some form of detection such as fluorescence may be used to detect the resulting DNA or 'DNA amplicon'. The change in fluorescence is directly proportional to the change in the quantity of target DNA. The number of cycles required to reach the pre-determined fluorescence threshold is compared to a standard that corresponds to the specific DNA target. A standard is typically the target gene that is pure and of known quantity at concentrations that span several logs. The number of copies of target DNA present in the sample is calculated using the standard curve. The copy number per sample is then used to determine the number of cells per sample.

In at least one embodiment a primer set is used which targets DNA sequences from bacteria using a conservative approach to quantify total bacteria. In at least one embodiment a primer set is used which targets primary biofilm-forming bacteria, including *Meiothermus*, *Pseudoxanthomonas*, and *Deinococcus*. In at least one embodiment a primer set is used to target an adaptive biofilm-former which belongs to the Sphingomonadacea family of bacteria. In at least one embodiment the adaptive biofilm-former exhibited higher tolerance to oxidant-based biocontrol programs compared to other biofilm and planktonic microorganisms. In at least one embodiment the primer is used to distinguish between fungal and bacterial infestations.

In at least one embodiment the process system involves materials passing into and out of shower streams and liquid basins containing various microorganisms from which live samples can be easily obtained. Sometimes however the process system is a dynamic environment including but not limited to such changes as transitioning between wet and dry conditions, have rapid passing through of air and liquids, and have drastic changes in pH temperature, salinity, light, rheology, viscosity, hydrophobicity, hydro-felicity, and shape/orientation (such as bending, flexing, rolling, etc. . . . ) and any combination thereof. As a result, the population of organisms inhabiting the sample at a given point in the process stream may differ from those present within the water sources or application devices such as shower streams and liquid basin. As a result a typical analysis of the shower streams and liquid basins will not correctly identify what microorganisms are present within the sample. An analysis of a sample which takes into account the sorts of organisms which are known to be able to inhabit those environments however allows for a truly accurate analysis of sample contaminations.

In at least one embodiment the method involves distinguishing between microorganisms at a category level such as the Domain Level. Biological life can be categorized according to one of three domains: Archaea, Bacteria, and Eukarya. Similarly the method involves distinguishing between microorganisms at the category of the biological kingdom level. Biological life can be categorized according to five kingdoms: Monera, Protist, Plant, Animal, and Fungus. Organisms in these different categories have hugely differing DNA and a protocol which focuses on identifying the organism's DNA at one of those distinctions is vastly simpler than more specific determinations. Because with samples, the organisms from categories are often best treated differently, such a simple form of identification can be used to accurately identify the specific regimen best targeted to the particular contaminant.

In at least one embodiment more than one primer is used to identify organisms that have more than one uniquely recognizable nucleotide sequence. In at least one embodiment the PCR analysis is used to detect genome sequences associated with enzymes unique to or nearly unique to specific organisms.

In at least one embodiment the method involves detecting a defect and then utilizing the PCR analysis to properly associate the source of the defect. In at least one embodiment the method determines if the defect is totally biologically based, totally non-biologically chemical based, or resulting from a combination of non-biologically chemical, mechanical, and biologically based sources.

In at least one embodiment the defect in the sample is one or more of: a hole, a hole with a discolored halo around at least a portion of it, a streak of discoloration, a spot, a translucent spot, and any combination thereof.

In at least one embodiment a threshold level is methodology used to discount false positives. Sometimes PCR analysis detects traces of organisms that while present are not causes of a particular defect. In at least one embodiment the method involves discounting the presence of any organism detected at a concentration lower than a pre-determined level known for one or more particular organisms. In at least one embodiment the method involves discounting the presence of any organism detected at level lower than $10^4$ cells per gram (of the defect). In at least one embodiment the method involves discounting the presence of any organism detected at level lower than $10^4$ cells per ml.

In at least one embodiment the results of the analysis are used to augment the biocontrol program by determining how much, what kind, and how often, one or more biocidal compositions are added to one or more locations within a water process system.

In at least one embodiment the method is able to detect microorganisms that would not otherwise be detected by prior art methods. For example in cases where foulant is caused by an infestation of anaerobic or sulfate reducing organisms, methods such as ORP detection would not correctly identify the foulant source as biological and would therefore incorrectly suggest applying an chemical not an anti-bilogical approach. Utilizing the DNA approach would however always correctly indicate a biological infestation because all life contains DNA.

In at least one embodiment a method is used for assessing microbial diversity. The method may be based on analysis of nucleic acids in sample extracts. More specifically, it utilizes PCR such as but not limited to qPCR for the detection of total organisms such as bacteria; *Sphingomonas* species; *Erythrobacter* species; *Pseudomonas* species; *Burkholderia* species; *Haliscomenobacter* species; *Saprospira* species; *Schlegelella* species; *Leptothrix* species; *Sphaerotilus natans; Bacillus* species; *Anoxybacillus* species; members of the Cytophaga-Flavobacterium-Bacteroides phylum; green nonsulfur bacteria, including *Herpetosiphon,* members of the Deinococcus-Thermus phylum, including *Meiothermus* species; catalase-producing bacteria, amylase-producing bacteria, urease-producing bacteria, fungi, etc. These techniques utilize primers and standards pairs that allow for detection and quantification of target organisms based on conserved sequences. The primers target regions in the microbial genome that are highly conserved through evolution, while primers for specific phyla or genera target more variable regions of the genome.

Being able to accurately quantify an organism of interest present in a sample makes it possible to express that organism as a percentage of the total bacterial load in the sample. Given the large number of organisms that can be detected, a snapshot of the diversity of the microbial population in sample can be determined. This snapshot is called the diversity index. The diversity index can also be expressed quantitatively as the relative abundance of several target organisms. The diversity index for any part of a process can be measured at times when machines or processes are running well, thus creating a baseline. The diversity index measured at times of poor machine or process performance can then be compared to the baseline to look for fluctuations in microbial populations and to determine which bacterial groups are responsible for problems in the process. The diversity index can also be quantified for ease of comparison using the Shannon diversity index calculation to compare monitoring data among sample locations or relative to a baseline. Treatment strategies and feed points can then be altered accordingly to combat the problem.

A diversity index based on quantification of DNA measures the presence and diversity of organisms in a process, independent of their viability. Ribonucleic acid (RNA), specifically messenger RNA (mRNA), is a molecule that is produced only by living organisms, and has properties such that, depending on the target, are unique to a specific phylum or genera of bacteria. By amplifying mRNA sequences that are unique to the organisms listed above it becomes possible to determine which bacteria are present in their viable form. Accurate detection of viable organisms can then be used as a tool for assessing the efficacy of treatment strategies of process waters. This can be accomplished by comparison of the diversity index to the viability index.

This method would quantify the amount and type of viable bacteria present in process samples. The quantitative (real time) polymerase chain reaction method can be applied to detect messenger ribosomal nucleic acids (mRNA). mRNA is transcribed DNA that is sent to the ribosome to serve as a blueprint for protein synthesis in a process known as translation. mRNA is produced only by living cells. RNA from living cells can be isolated with the use of commercially available kits. Detection of mRNA requires an extra step in the quantitative polymerase chain reaction. Reverse transcriptase is added to the reaction cocktail to transcribe mRNA into its complementary DNA (cDNA). Two sets of primers are required for this experiment. The first targets specific mRNA, while the second is used to amplify the resulting cDNA produced by the reverse transcriptase reaction.

EXAMPLES

The foregoing may be better understood by reference to the following examples, which are presented for purposes of illustration and are not intended to limit the scope of the invention. In particular the examples demonstrate representative examples of principles innate to the invention and these principles are not strictly limited to the specific condition recited in these examples. As a result it should be understood that the invention encompasses various changes and modifications to the examples described herein and such changes and modifications can be made without departing from the spirit and scope of the invention and without diminishing its intended advantages. It is therefore intended that such changes and modifications be covered by the appended claims.

Threshold Value Determination Example

An uncoated freesheet mill was suffering from a felt permeability problem on one of its paper machines. The permeability of the felt fabrics on one of the machines at the mill decreased at a significantly greater rate than on the other two machines. All chemical means to resolve this problem were exhausted and the mill began to look toward microbial contamination as a possible problem. However, the mill's biocontrol program was perceived to be running well due to low bacterial counts, low ATP measurements, and lack of slime deposition on machine surfaces.

In order to solve this problem, felt samples from the unaffected machine were compared to those from the struggling machine using qPCR (FIG. 1). While both felts contained the same amount of total bacteria ($\sim 10^7$ cells/g), it was immediately obvious that the problematic felt had a bacterial population that was dominated by a single group of organisms: adaptive biofilm formers. These bacteria were present in small amount on the other felt.

Figure 2:
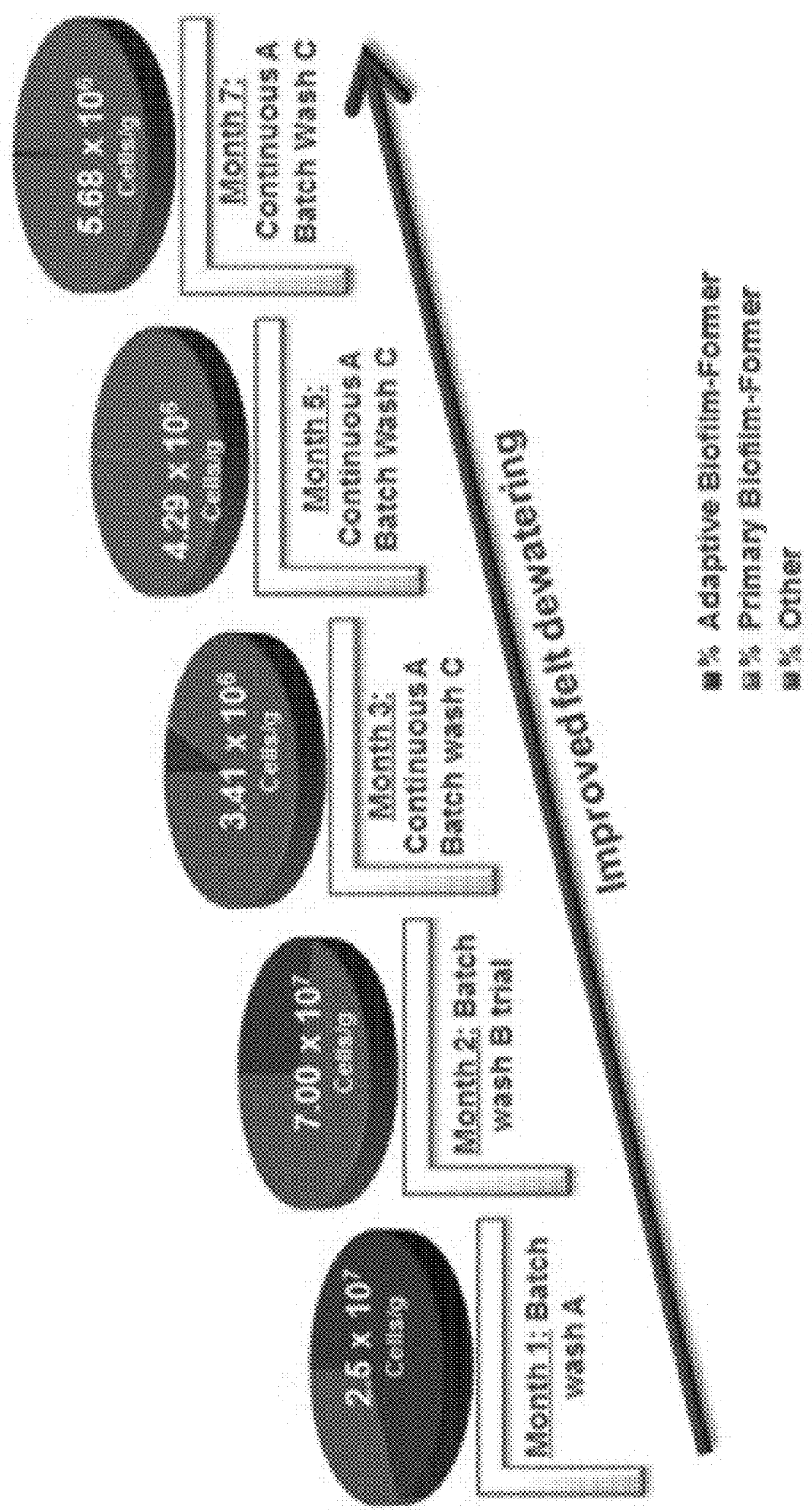
FIG. 2 illustrates pie charts of relative abundance of bacteria in felt fabrics over time as determined by qPCR. The numbers over the pie graphs represent total bacterial loading of the sample.

Following the discovery of a dominant bacterial population growing in the felt, the felt cleaning chemical was changed. The fabric was reanalyzed during the subsequent shutdown period. It was observed that the adaptive biofilm former population was reduced to 25% of the total population, with the overall bacterial load remaining unchanged (FIG. 2).

Figure 3:
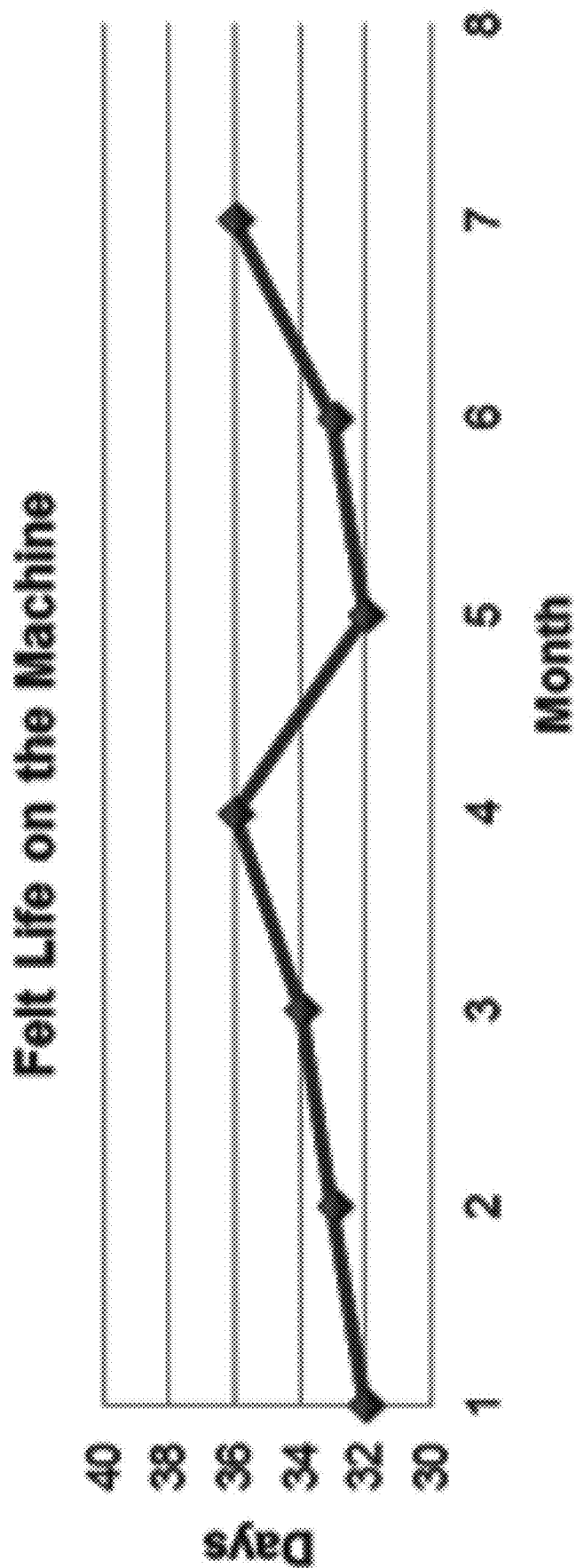
FIG. 3 is a graph illustrating felt fabric lifetime (in days) on the machine before (Month 1) and during (Months 2-7) program optimization.

Based on these data, a second chemical, shown to have good efficacy against the adaptive biofilm formers, was added to the felt washing protocol. After this second chemistry adjustment, the felts were reanalyzed during a shutdown period. DNA results showed that the total bacterial load stayed unchanged, while the adaptive biofilm formers were reduced to roughly 10% of the total population (FIG. 2). The new chemistry combination was allowed to run on the machine for the next four months. Over the course of these months, the adaptive biofilm former population was eliminated from the felt fabrics on this machine. The elimination of this group of bacteria resulted in improvement in dewatering efficiency of the felts, and the extension of the life of the fabrics by 4 days (FIG. 3).

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments mentioned herein, described herein and/or incorporated herein. In addition the invention encompasses any possible combination that also specifically excludes any one or some of the various embodiments mentioned herein, described herein and/or incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range. All percentages, ratios and proportions herein are by weight unless otherwise specified.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method of detecting a microorganism-caused problem in a water process system, the method comprising:
    measuring an overall microorganism population in at least a portion of the water process system of a paper mill wherein the water in the water process system comprises feed water from a feed water input outside of the water process system;
    identifying at least one subgroup of microorganism population in the overall microorganism population;
    measuring an amount of the at least one subgroup of microorganism population relative to the overall microorganism population to determine a relative abundance of the at least one subgroup of microorganism population;
    determining that the relative abundance of the at least one subgroup of microorganism population exceeds a predetermined threshold, wherein the predetermined threshold is that the at least one subgroup of microorganism population is present in an amount of at least 5-90% of the overall microorganism population;
    measuring a feed water microorganism population in the feed water input;
    comparing the relative abundance of the at least one subgroup of microorganism population in the portion of the water process system with the amount and type of bacteria in the feed water microorganism population in the feed water input;
    identifying the feed water input as the source of the at least one subgroup of microorganism population in the water process system; and
    applying a bio-control procedure to the feed water input before the feed water of the feed water input enters the water process system to reduce the amount of the at least one subgroup of microorganism population.

2. The method of claim 1, in which the at least one subgroup of microorganism population comprises filamentous bacteria.

3. The method of claim 1, in which the at least one subgroup of microorganism population is selected from the group consisting of *Spirogyra, Cladophora, Pithophora, O. Siphonocladales pithophora pithophora, Ulvibacter litoralis, Vetellibacter vladivostokensis, Weeksella virosa, Fucobacter, Gelidbacter, Ornithobacterium rhinotracheale, Riemerella cohambina, Flavobacterium psychrofilum, Herpetosiphon, Haliscomenobacter, Sphaerotilus, Ctyophaga succinicans, Vladibacter, Pfeifferella, Bacillus aquatilllis, Flexibacter marinus, Flavobacterium odoratum, Microscilla, Flexithrix, Capnocytophaga, Taxeobacter, Sporocytophaga, Saprospira, Chryseobacterium, Hymenobacter,* and any combination thereof.

4. The method of claim 1, wherein the feed water input is selected from the group of municipal water, tap water, pond water, sea water, lake water, filtered water, desalinated water, recirculated water, wastewater, distilled water, condensed boiler water, cooling water, and any combination thereof.

5. The method of claim 1, in which at least one measurement is taken by one process selected from the list consisting of: Chain Termination Sequencing, Denaturing Gradient Gel Electrophoresis (DGGE), Digital Polymerase Chain Reaction, DNA Based Analysis, Ion Torrent Semiconductor Sequencing, MALDI, MALDI-TOF, Mass Spectrometry, PCR Analysis, Pyrosequencing, qPCR Analysis, Sequencing by Oligonucleotide Ligation and Detection, Sequencing by Synthesis, measurement of antibodies associated with one or more microorganisms, measurement of hormones associated with one or more microorganisms, measurement of secretions associated with one or more microorganisms, measurement of proteins associated with one or more microorganisms, measurement of organic molecules associated with one or more microorganisms, measurement of molecules associated with one or more microorganisms, fluorescent phages, cell sorters, and any combination thereof.

6. The method of claim 1, further comprising recording the at least one identified subgroup of microorganism population into a format which can be stored and/or transmitted.

7. The method of claim 1, in which at least one measurement is taken from a sample product of the water process system.

8. The method of claim 7, wherein the sample product has little or no organisms living on it.

9. The method of claim 1, wherein the at least one subgroup of microorganism population comprises biofilm-forming bacteria.

10. The method of claim 1, further comprising conducting subsequent analysis to confirm that the bio-control procedure has reduced the amount of the at least one subgroup of microorganism population below the predetermined threshold.

11. The method of claim 1, wherein the predetermined threshold is that the at least one subgroup of microorganism population is measured to be at least 10% of the overall microorganism population.

12. The method of claim 1, in which at least one measurement is taken from a felt fabric of a paper machine, the paper machine utilizing the water process system.

13. A method of treating a microorganism caused problem in a water process system, the method comprising:

determining a threshold at which a rise in amount of at least one subgroup of microorganism population relative to an overall microorganism population warrants a change in bio-controls of at least a portion of a water process system of a paper mill wherein the water in the water process system comprises feed water from a feed water input outside of the water process system;

measuring a relative abundance of the at least one subgroup of microorganism population relative to the overall microorganism population in a sample taken from a deposit on equipment surface, water, fluid sample, or whole pieces or partial fragments of intermediate or end stage products of the water process system;

determining that the relative abundance of the at least one subgroup of microorganism population exceeds the threshold in at least a portion of the water process system;

measuring a feed water microorganism population in at least a portion of the feed water input;

comparing the relative abundance of the at least one subgroup of microorganism population in the portion of the water process system with the amount and type of bacteria in the feed water microorganism population in the feed water input;

identifying the feed water input as a source of the at least one subgroup of microorganism population;

applying a bio-control procedure to the feed water input before the feed water of the feed water input enters the water process system to reduce the amount of the at least one subgroup of microorganism population in the feed water input in which the relative abundance of the at least one subgroup of microorganism population exceeds the threshold; and measuring the relative abundance of the at least one subgroup of microorganism population after applying the bio-control procedure to confirm that the bio-control procedure is reducing the relative abundance of the at least one subgroup of microorganism population in at least the portion of the water process system.

14. The method of claim 13, wherein the at least one subgroup of microorganism population is selected from the group consisting of *Spirogyra, Cladophora, Pithophora, O. Siphonocladales pithophora pithophora, Ulvibacter litoralis, Vetellibacter vladivostokensis, Weeksella virosa, Fucobacter, Gelidbacter, Ornithobacterium rhinotracheale, Riemerella cohambina, Flavobacterium psychrofilum, Herpetosiphon, Haliscomenobacter, Sphaerotilus, Ctyophaga succinicans, Vladibacter, Pfeifferella, Bacillus aquatilllis, Flexibacter marinus, Flavobacterium odoratum, Microscilla, Flexithrix, Capnocytophaga, Taxeobacter, Sporocytophaga, Saprospira, Chryseobacterium, Hymenobacter,* and any combination thereof.

15. The method of claim 13, wherein the feed water input is selected from the group of municipal water, tap water, pond water, sea water, lake water, filtered water, desalinated water, recirculated water, wastewater, distilled water, condensed boiler water, cooling water, and any combination thereof.

* * * * *

UNITED STATES PATENT AND TRADEMARK OFFICE
CERTIFICATE OF CORRECTION

Page 1 of 1

PATENT NO. : 11,608,516 B2
APPLICATION NO. : 14/687017
DATED : March 21, 2023
INVENTOR(S) : Laura E. Rice It is certified that error appears in the above-identified patent and that said Letters Patent is hereby corrected as shown below:

On the Title Page

Item [57], Column 2, Line 3: "potion" should read "portion"

In the Claims

Column 15, Line 5: In Claim 3, "Fucobacter" should read "Fusobacterium"

Column 15, Line 9: In Claim 3, "aquatillis" should read "aquatilis"

Column 16, Line 46: In Claim 14, "Fucobacter " should read "Fusobacterium"

Column 16, Line 50: In Claim 14, "aquatillis" should read "aquatilis"

Signed and Sealed this
Seventh Day of January, 2025

Derrick Brent
*Acting Director of the United States Patent and Trademark Office*